US008333993B1

(12) United States Patent
Perez et al.

(10) Patent No.: US 8,333,993 B1
(45) Date of Patent: *Dec. 18, 2012

(54) SYNTHESIS OF POLYMER COATED CERIA NANOPARTICLES FOR BIOMEDICAL APPLICATIONS

(75) Inventors: Jesus Manuel Perez, Orlando, FL (US); Atul Asati, Orlando, FL (US); Sudip Nath, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 973 days.

This patent is subject to a terminal disclaimer.

(21) Appl. No.: 11/965,343

(22) Filed: Dec. 27, 2007

Related U.S. Application Data

(60) Provisional application No. 60/878,043, filed on Dec. 29, 2006.

(51) Int. Cl.
*A61K 9/14* (2006.01)

(52) U.S. Cl. ...................................................... 424/489

(58) Field of Classification Search .................... None
See application file for complete search history.

(56) References Cited

U.S. PATENT DOCUMENTS

| | | | |
|---|---|---|---|
| 2003/0124194 | A1 | 7/2003 | Gaw et al. |
| 2005/0130167 | A1 | 6/2005 | Bao et al. |
| 2006/0014938 | A1* | 1/2006 | Groman et al. ................ 534/15 |
| 2006/0142749 | A1 | 6/2006 | Ivkov |
| 2010/0166821 | A1* | 7/2010 | Rzigalinski et al. .......... 424/423 |

FOREIGN PATENT DOCUMENTS

WO    WO03005029    1/2003

OTHER PUBLICATIONS

Sathyamurthy et al ("Reverse micellar synthesis of cerium oxide nanoparticles," Nanotechnology 16 (2005) 1960-1964).*
Srivatsan Sathyamurthy, et al., "Reverse Micellar Synthesis of Cerium Oxide Nanoparticles" Nanotechnology, 16 (2005) pp. 1960-1964.
S. Patil, et al., "Synthesis of Nanocrystalline Ceria Particles for High Temperarture Oxidation Resistant Coating" Journal of Nanoparticle Research, 4, (2002) pp. 433-438.
H.S. Potdar, et al. "Preparation of ceria-ziconia (Ce0.75Zr0.25O2) powders by microwave-hydrothermal (MH) route" Material Chemistry and Physics, 74, (2002) pp. 306-312.
David Schubert, et al., "Cerium and yttrium oxide nanoparticles are neuroprotective" Biochmical and Biophysical Research Communications, 342, (2006) pp. 86-91.
Mukesh G. Harisinghani et al., "Noninvasive Detection of Clinically Occult Lymph-Node Metastases in Prostate Cancer" New England Journal of Medicine, vol. 348, No. 25, (Jun. 19, 2003) pp. 2491-2500.

* cited by examiner

*Primary Examiner* — Suzanne Ziska
(74) *Attorney, Agent, or Firm* — Brian S. Steinberger; Joyce Morlin; Law Offices of Brian S. Steinberger, P.A.

(57) ABSTRACT

Procedures and methods for synthesizing biodegradable polymer coated nanoceria result in stable nanoparticle preparations in aqueous systems and physiological relevant colloidal solutions, such as phosphate buffer saline. The coated nanoceria preparations increase the nanoparticle concentration in aqueous or colloidal solutions as most needed for antioxidant, free-radical scavenger, and autocatalytic biomedical applications, including, biological, pharmacological and potential clinical use. To meet this need, a facile synthetic procedure for preparation of a biodegradable polymer-coated nanoceria is disclosed; the preferred biodegradable polymer is dextran. The synthesis method occurs under ambient conditions in an aqueous phase without the use of surfactants and results in a monodispersed preparation that is dextran-coated as determined by dynamic light scattering (DLS). Preliminary characterization of polymer coated nanoceria by XPS, TEM, XRD, and the like shows that these nanoparticles have the necessary physical properties for the desired biological potency, such as $Ce^{+4}/Ce^{+3}$ mixed valence state.

25 Claims, 14 Drawing Sheets

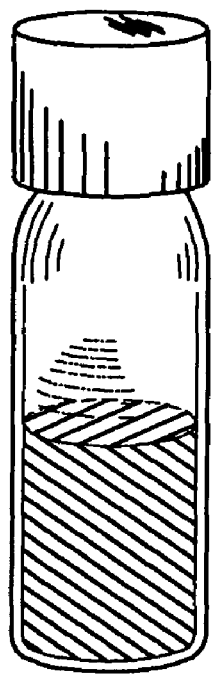 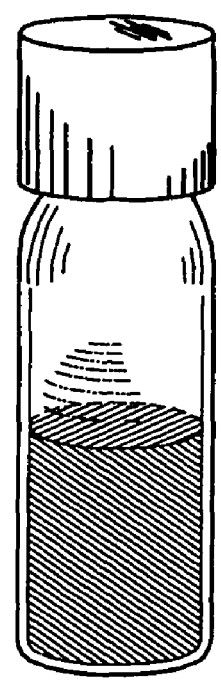
Fig. 6A
Photographic image of a first solution of dextran coated nanoceria.
Fig. 6B
Photographic image of a second solution of dextran coated nanoceria.

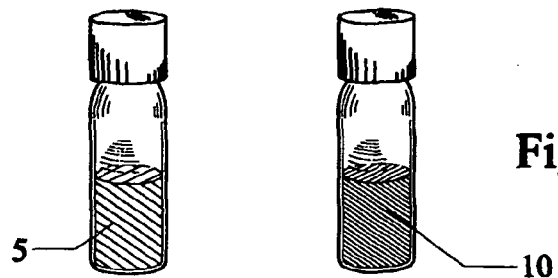
Fig. 10A (Day 1)
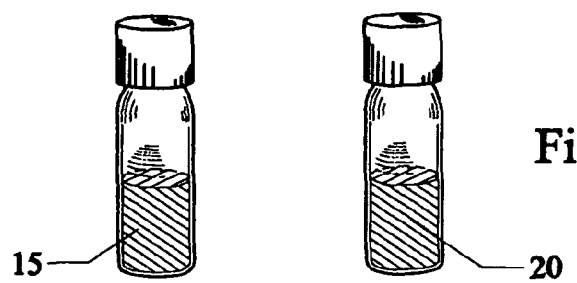
Fig. 10B (Day 3)
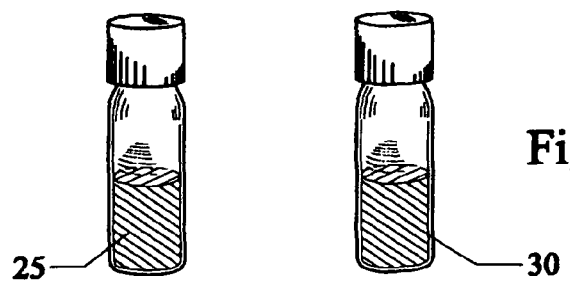
Fig. 10C (Day 7)
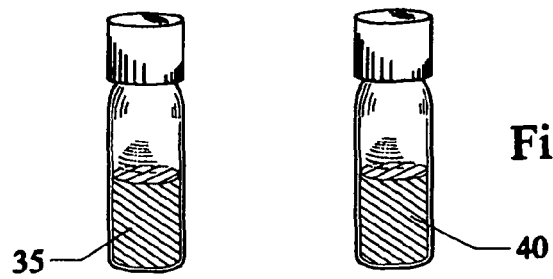
Fig. 10D (Day 10)

Fig. 10E
After adding fresh hydrogen peroxide on 10th day
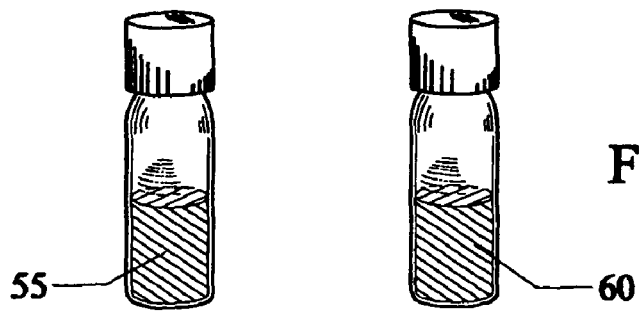
Fig. 10F (Day 20)

United States Patent US 8,333,993 B1

SYNTHESIS OF POLYMER COATED CERIA NANOPARTICLES FOR BIOMEDICAL APPLICATIONS

The present application claims the benefit of priority from U.S. Provisional Patent Application Ser. No. 60/878,043 filed on Dec. 29, 2006, which is incorporated herein by reference.

FIELD OF THE INVENTION

This invention relates to biological uses of nanoceria particles, and in particular to methods and compositions useful in the synthesis of polymer coated ceria oxide nanoparticles for biomedical applications.

BACKGROUND AND PRIOR ART

Cerium is a silvery metallic element, belonging to the lanthanide group. Cerium oxide ($CeO_2$) is used in precision polishing and lapping applications. Ultra fine nano-size cerium oxide, less than 10 nanometers, is more efficient for coating purposes. Recently, it was reported by B. Rzigalinski et al. that nanoparticles prolong the life of cortical neurons in culture 4 fold over the cells without treatment, decrease the intracellular $Ca^{2+}$ concentration and prevent UV damage of cortical neurons. See B. Rzigalinski et al., "Cerium Oxide Nanoparticles Extend Cell Longevity and Act as Free Radical Scavengers" at website www.med.miami.edu/mnbws/Rzigalinski 112. Based on its chemical characteristics, this effect is partially due to a decrease of reactive oxygen species (ROS).

Various investigators have shown that nanoceria particles possess antioxidant properties and have demonstrated survival of neuron cells in cultures against oxidative stress and radiation. The greatest benefit of the nanoceria is its ability to get inside the cells and provide protection from reactive oxygen species (ROS); other body systems and tissues can also be protected from damage due to ROS.

However, the synthetic procedures for nanoceria reported so far are not likely to be approved by the U.S. Food and Drug Administration (FDA) because the synthesis procedures involve the use of surfactants and other toxic materials.

In addition to the use of non-approved surfactants and toxic materials, the published synthetic methods result in uncoated nanoparticles which agglomerate in aqueous solution.

Further developments in biomedical research reveal the efficacy of coated magnetic nanoscale particle compositions for therapeutic uses. In Patent Publication WO/2003/005029 to Zhenghe Xu et al. iron and iron oxide particles are coated with dextran for biological cell separation using magnetic carrier technology. The dextran coating is used to prevent mechanical instability of the particle in suspension.

U.S. Patent Publication 2003/0124,194 to Gaw et al. discloses amine functionalized superparamagnetic nanoparticles using a process that consists of coating magnetic nanoparticles with a carboxylated polymer then subsequently reacting the carboxylated functionalized magnetic nanoparticles with carbodiimide and a large excess of diamine, after which the amine-terminated nanoparticles are reacted with bifunctional crosslinking agents and with various biomolecules.

U.S. Patent Publication 2005/0130167 to Gang Boa, et al. provides multifunctional magnetic nanoparticle probe compositions for molecular imaging and monitoring wherein the magnetic nanoparticle has a biocompatible coating, such as, dextran, thereon.

U.S. Patent Publication 2006/0014938 to Groman et al. describes stable aqueous colloidal lanthanide oxides, including cerium oxide, some of which are associated with a polymer, including dextran. The colloidal compositions are useful as imaging agents in technology requiring injectable chemicals for contrast agents. There is no mention of cerium oxide coated with polymers having autocatalytic and antioxidant properties.

U.S. Patent Publication 2006/0142749 to Robert Ivkov discloses thermotherapeutic compositions for treating disease. The thermotherapeutic compositions include magnetic nanoparticles that may be coated to enhance the heating properties of a bioprobe, particularly if the coating is a polymeric material that can include dextran.

Thus, polymeric coatings including dextran have been reported for use on magnetic nanoparticles and the results seem promising in molecular imaging, monitoring and therapeutic treatment of disease.

It is desirable to find reliable solutions to use of nanoceria particles with antioxidant properties in the treatment of many human diseases that are due to the death of cells in specific tissues or organs. The majority of those diseases are due to accumulation of metabolic insults from reactive oxygen species originating within or outside of the cells. These diseases include all forms of blindness whether hereditary, light-induced, or physical damage such as occurs in retinal detachment. In addition, damage due to ageing, stroke, cardiac infarction, burns, etc, which proceed through reactive oxygen species, can be addressed with the nanoceria particles synthesized according the present invention.

SUMMARY OF THE INVENTION

A primary objective of the present invention is to provide a facile, synthetic method for the formation of cerium oxide (ceria) nanoparticles coated with a biodegradable polymer.

A secondary objective of the present invention is to provide a synthetic method for the formation of cerium oxide (ceria) nanoparticles coated with dextran, a biodegradable polymer that can be scaled up for commercial production.

A third objective of the present invention is to provide cerium oxide (ceria) nanoparticles coated with a biodegradable polymer that has physical properties that are substantially identical of the properties of uncoated nanoceria particles for therapeutic applications.

A fourth objective of the present invention is to provide cerium oxide (ceria) nanoparticles coated with a biodegradable polymer with good solubility and stability in water and phosphate buffer saline.

A fifth objective of the present invention is to provide a facile, synthetic method for the formation of cerium oxide (ceria) nanoparticles coated with dextran that is further crosslinked with epichlorohydrin and ammonia, resulting in an aminated dextran coated ceria nanoparticles to create a targetable ceria nanoparticle.

A sixth objective of the present invention is to provide a water stable, biodegradable polymer coated nanoceria preparation that is biologically active for administration to human and other mammals.

A seventh objective of the present invention is to provide a water stable, biodegradable polymer coated nanoceria preparation that has a long circulation time, such as, a plasma half-life longer than one minute.

An eighth objective of the present invention is to provide a facile, synthetic method for the formation of cerium oxide (ceria) nanoparticles coated with polyacrylic or any other polycarboxylic acid polymer that will result in a carboxyl group functionalized nanoparticle. The ceria nanoparticles coated with functionalized carboxyl groups are reacted with a diamine, such as ethylenediamine, to create an amine functionalized cerium oxide nanoparticle without the need for polymeric crosslinking.

A preferred method for the synthesis of a plurality of cerium oxide nanoparticles coated with a biodegradable polymer for antioxidant, free-radical scavenging and autocatalytic biomedical applications, includes preparing an aqueous cerium nitrate solution, mixing the aqueous cerium nitrate solution with a biodegradable polymer to form a first mixture, adding the first mixture dropwise to an ammonium hydroxide solution while continuously stirring to form a second mixture, centrifuging the second mixture containing ammonium hydroxide to settle any debris or large particles, purifying the centrifuged mixture by ultrafiltration, and recovering a plurality of non-agglomerated cerium oxide nanoparticles coated with the biodegradable polymer wherein the antioxidant, free-radical scavenging and autocatalytic properties of the cerium oxide nanoparticles are unchanged from uncoated cerium oxide nanoparticles.

The preferred synthesis method has a biodegradable polymer that is at least one of a carbohydrate polymer, a synthetic polyol, a carboxylated polymer, and derivatives thereof, more preferably, the carboxylated polymer is polyacrylic acid.

It is also preferred that the carboxylated polymer is reacted with a diamine selected from at least one of ethylene diamine, propylene diamine and hexane diamine, to provide an aminated cerium oxide nanoparticle in a reaction that eliminates the need for polymer crosslinking.

The preferred carbohydrate polymer for the synthesis method of the present invention is a polysaccharide, such as dextran, arabinogalactan, chitosan and the like; most preferably the polysaccharide is dextran.

In the preferred synthesis method the cerium nitrate solution contains approximately 2.0 to approximately 3.0 grams of cerium nitrate to approximately 5 ml of water and the plurality of dextran-coated cerium oxide nanoparticles has a UV profile exhibiting strong absorption below approximately 400 nm with peak absorption at approximately 300 nm.

A preferred composition that is useful as a potent antioxidant in biomedical applications includes a plurality of nanoceria particles coated with a biodegradable polymer selected from at least one of a carbohydrate polymer, a synthetic polyol, a carboxylated polymer, and derivatives thereof. The more preferred carboxylated polymer is polyacrylic acid. The preferred carbohydrate polymer is a polysaccharide, such as, dextran, arabinogalactan and chitosan; most preferably, the polysaccharide is dextran.

In the preferred composition, the plurality of dextran-coated cerium oxide nanoparticles has a UV profile exhibiting strong absorption below approximately 400 nm with peak absorption at approximately 300 nm and the physical properties of the dextran-coated cerium nanoparticles replicate the physical properties of the uncoated nanoceria particles for therapeutic applications as antioxidants, free-radical scavengers and autocatalytic agents.

In the preferred composition, the plurality of dextran-coated cerium oxide nanoparticles form a colloidal suspension that is stable in water and form a colloidal suspension that is stable in a phosphate buffer saline solution.

A more preferred composition of matter that is useful as an antioxidant, free-radical scavenger and autocatalyst in biomedical applications includes a plurality of nanoceria particles coated with a crosslinked-aminated biodegradable polymer selected from at least one of a carbohydrate polymer, a synthetic polyol, a carboxylated polymer, and derivatives thereof. The preferred carbohydrate polymer is a polysaccharide such as, dextran, arabinogalactan and chitosan; the most preferred polysaccharide is dextran.

The preferred composition has a plurality of dextran-coated cerium oxide nanoparticles with a UV profile exhibiting strong absorption below approximately 400 nm with peak absorption at approximately 300 nm and the physical properties of the dextran-coated cerium nanoparticles replicate the physical properties of the uncoated nanoceria particles for therapeutic applications as antioxidants, free-radical scavengers and autocatalytic agents.

The more preferred composition has a plurality of dextran-coated cerium oxide nanoparticles that form a colloidal suspension that is stable in water and also form a colloidal suspension that is stable in a phosphate buffer saline solution.

Further objects and advantages of the present invention will be apparent from the following detailed description of a presently preferred embodiment which is illustrated schematically in the accompanying drawings.

BRIEF DESCRIPTION OF THE FIGURES

FIG. 6A is a photographic image of a first solution of dextran coated nanoceria after ultrafiltration with an Amicon 30 K filter.

FIG. 6B is a photographic image of a second solution of dextran coated nanoceria after the solution is concentrated using a 30K Centricon concentrator.

FIG. 10A is a real-time image of dextran nanoceria solutions without hydrogen peroxide on the left and with hydrogen peroxide on the right at day one.

FIG. 10B is a real-time image of dextran nanoceria solutions without hydrogen peroxide on the left and with hydrogen peroxide on the right at day three.

FIG. 10C is a real-time image of dextran nanoceria solutions without hydrogen peroxide on the left and with hydrogen peroxide on the right at day seven.

FIG. 10D is a real-time image of dextran nanoceria solutions without hydrogen peroxide on the left and with hydrogen peroxide on the right at day ten.

FIG. 10E is a real-time image of dextran nanoceria solutions without hydrogen peroxide on the left and with hydrogen peroxide on the right at day ten after adding fresh hydrogen peroxide.

FIG. 10F is a real-time image of dextran nanoceria solutions without hydrogen peroxide on the left and with hydrogen peroxide on the right at day twenty.

DESCRIPTION OF THE PREFERRED EMBODIMENTS

Figure 1:
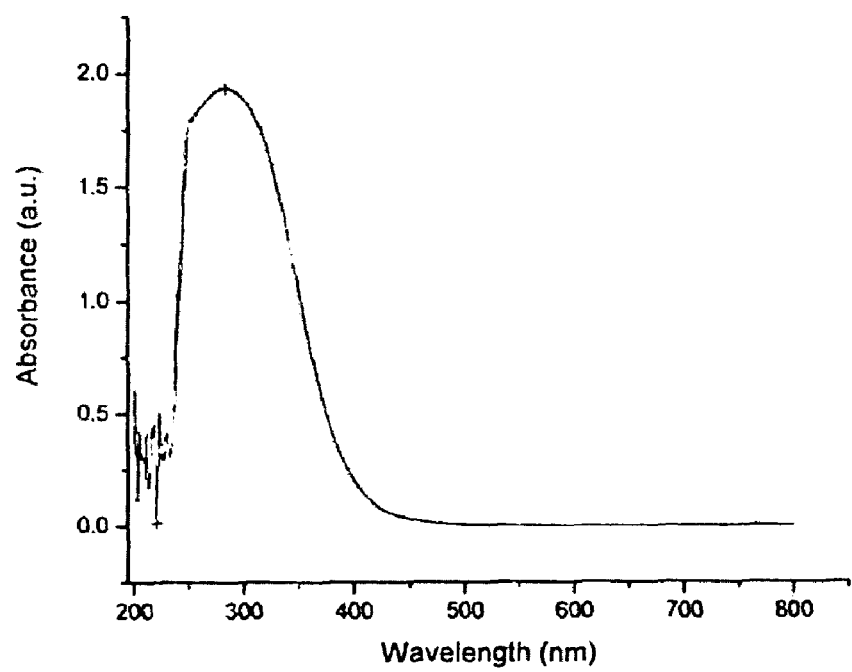
FIG. 1 shows the UV-visible absorption spectrum of the dextran coated nanoceria prepared in the present invention.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The term "nanoceria" is used interchangeably with "cerium oxide nanoparticles" and is used to refer to the cerium oxide particles of multiple valences.

The term "biodegradable polymer" is used herein to describe a class of polymers that are non-toxic to mammals and the environment and more specifically, include dextran, derivatives of dextran such as reduced dextran, carboxyl methyl reduced dextran, a polyol polymer or carbohydtrate polymer, synthetic polyols, carboxylated polymers, such as polyacrylic acid, and other polysaccharides, such as, but not limited to, arabinogalactan, and chitosan as disclosed in Groman et al. U.S. Patent Publication 2006/0014938 and Gaw et al. U.S. Patent Publication 2003/0124,194.

In the present invention, the cerium oxide nanoparticles or nanoceria are polymer associated, or, in other words, coated with a biodegradable polymer. The polymer confers stability in water and can be functionalized with carboxylic or amino groups for conjugation with proteins, peptides, oligonucleotides, small molecules, and the like.

In general, the polymer coated nanoceria particles of the present invention each have a size between approximately 1 nanometer (nm) to approximately 500 nm in diameter, preferably between approximately 1 nm and approximately 10 nm.

Methods of preparing the biodegradable polymer coated cerium oxide compositions for use as an antioxidant and protection from damaging ultra violet (UV) radiation are provided in detail below.

The first embodiment of the present invention provides a method and procedure for synthesizing a biodegradable polymer coated ceria nanoparticle for antioxidant and autocatalytic biomedical applications.

The second embodiment of the present invention provides a method and procedure for synthesizing aminated crosslinked dextran coated ceria nanoparticles for antioxidant and autocatalytic biomedical applications.

The third embodiment of the present invention provides a method and procedure for synthesizing non-crosslinked, carboxylated polymer coated ceria nanoparticles to provide an amine functionalized nanoparticle for antioxidant and autocatalytic biomedical applications.

The examples below provide further detail on the synthesis and physical characterization of the biodegradable polymer coated ceria nanoparticles of the present invention.

Example 1

Synthesis of Dextran Coated Ceria Nanoparticles

Under ambient conditions, a 1 M cerium nitrate solution (2.17 g in 5 ml of water) was mixed with a 1M Dextran T-10 (5 g in 10 ml of water) to form mixture (I). Under continuous stirring, the mixture (I) is then added dropwise to 30 ml of 29% ammonium hydroxide solution (Fischer, USA) forming mixture (II). Mixture (II) is then stirred continuously for 24 hours. After 24 hours of stirring, the solution turns from a light yellow to a deep brown color. The preparation is centrifuged at a rate of 4000 rpm for two 30-minute cycles to settle down any debris and large particles. The preparation is then purified from free dextran by ultrafiltration using a 30 K Amicon filter.

Example 2

Crosslinking and Amination of Dextran Coated Ceria with Epichlorohydrin

Dextran coated ceria nanoparticles are crosslinked with epichlorohydrin using following procedure under ambient conditions:

To 3 ml (3 volume) of dextran coated nanoceria particle preparation in Example 1, 5 mL (5 volumes) of 5M NaOH are added while stirring. Then, 2 mL (2 volumes) of epichlorohydrin are added to the stirring solution. The ceria nanoparticle suspension is stirred vigorously for 8 hours at room temperature. Then, 8.5 mL (8.5 volumes) of 30% ammonia is added and stirred overnight at room temperature. The next day, the excess epichlorohydrin and ammonia are removed by ultrafiltration and the nanoparticle buffer is exchanged to 0.025 M Na-Citrate buffer pH 8. At this point, the aminated dextran nanoceria preparation can be concentrated without precipitation of the nanoparticles.

Epichlorohydrin is used as the crosslinking agent in Example 2, however, it is understood by those skilled in the art that other crosslinking agents may be used, such as glutaraldehyde, bromide derivatives of cyanogens and the like.

It is a primary concern that the physical properties of the biodegradable polymer coated ceria nanoparticles remain unaffected by the coating which improves handling and application for biomedical purposes.

In FIG. 1, the UV profile for the dextran coated nanoceria is shown. Dextran coated ceria particles show strong absorption below 400 nm with peak absorption maximum at 300 nm. The UV profile of the dextran coated nanoceria prepared in the present invention is similar to that obtained in previous work showing that naked or uncoated ceria nanoparticles have well defined peak absorption around 305 nm. Thus, the UV profile of the coated and uncoated nanoceria is substantially the same.

Figure 2:
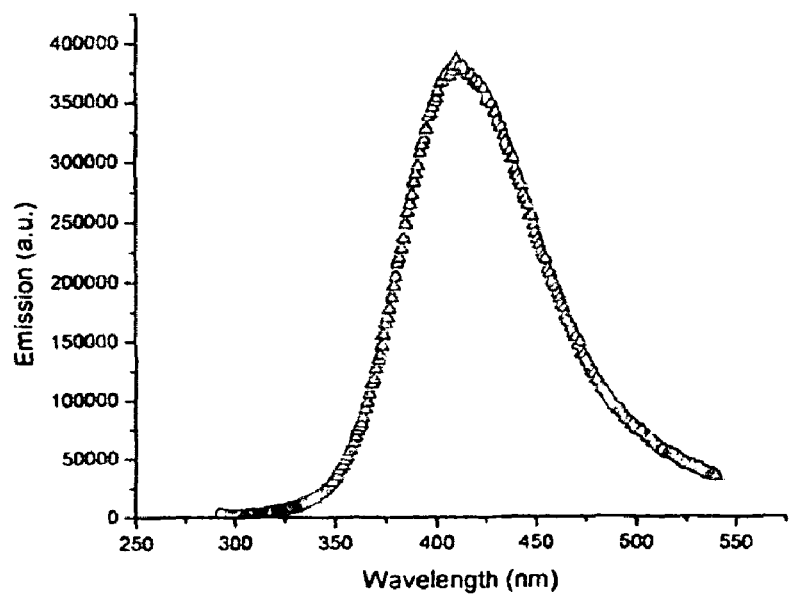
FIG. 2 is the fluorescence spectra of dextran coated cerium oxide nanoparticle ($\lambda_{ex}$=283 nm) showing a characteristic fluorescence peak at approximately 410 nanometer (nm) wavelength.

In FIG. 2 the fluorescence spectra of dextran coated nanoceria particles of the present invention has a characteristic fluorescence peak around 410 nm and is similar to the fluorescence spectra of the uncoated nanoceria particles reported by S. Sathyamurthy et al. in "Reverse Micellar Synthesis of Cerium Oxide Nanoparticles" *Nanotechnology* 16 (2005) 1960-1964.

Figure 3:
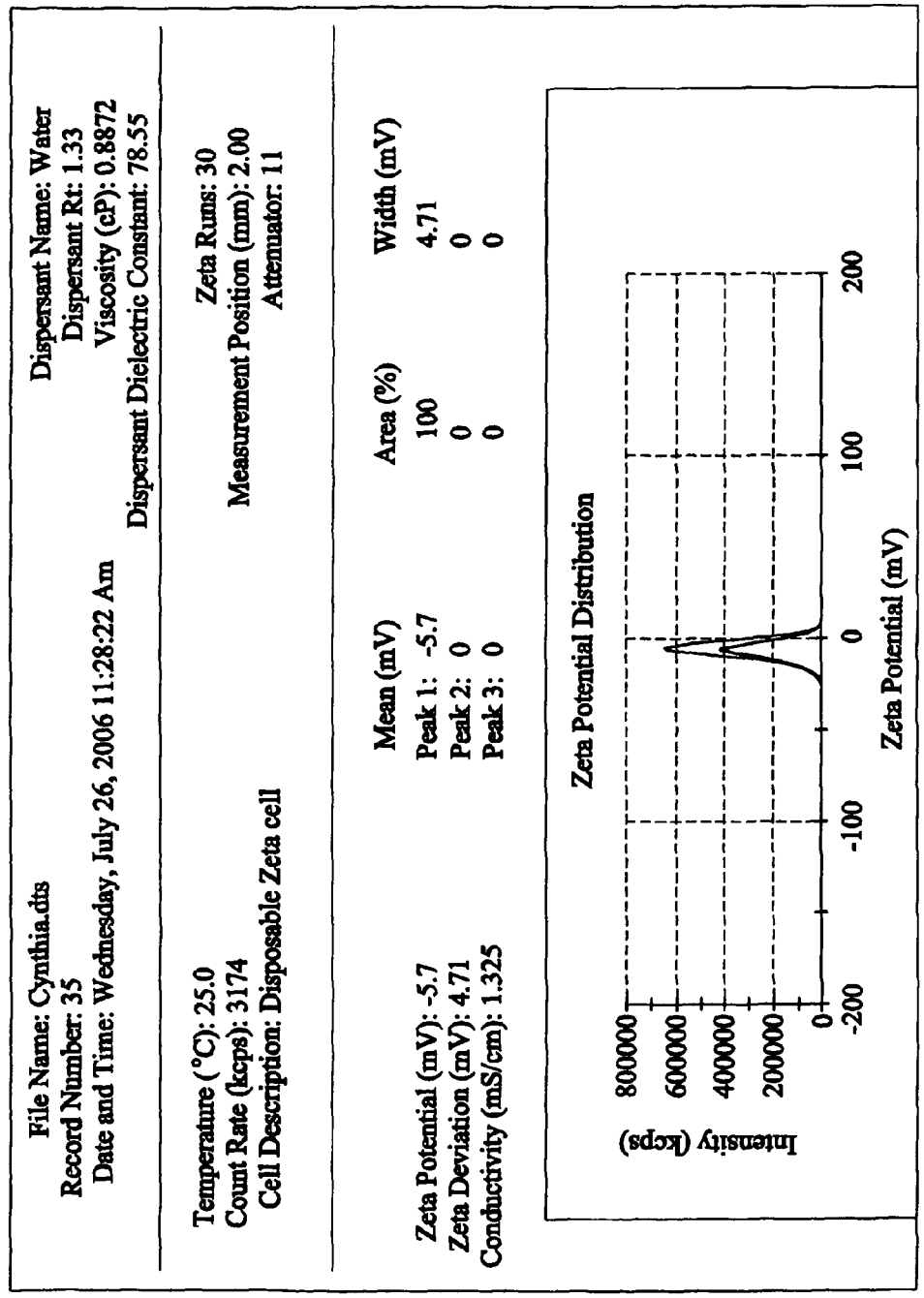
FIG. 3 shows the measurement of zeta-potential in the analysis of the stability of nanoparticle preparation against agglomeration within biological systems.

To analyze the stability of nanoparticle preparation against agglomeration within biological systems, zeta-potential measurement is performed. In pure water, the zeta-potential measurements of oxide dispersions cover a wide range from −25 to 55 mV. Due to the presence of dextran polymer on the surface of the nanoparticle, its charge distribution would be affected and the zeta potential would be shifted toward more positive and less negative values. The dextran coated nanoceria preparation of the present invention has a zeta potential of −5.7 mV as shown in FIG. 3.

Figure 4:
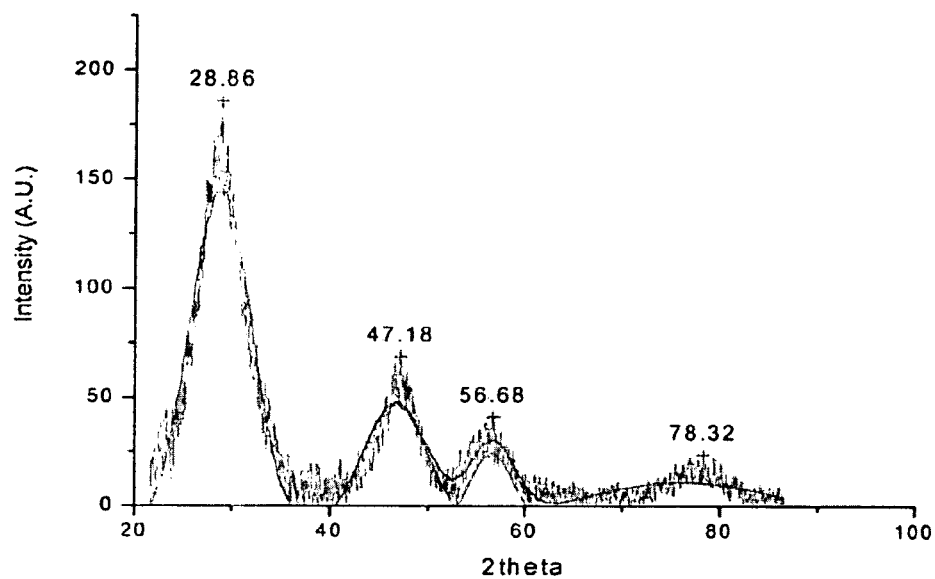
FIG. 4 shows the X-ray diffraction pattern of nanocrystalline cerium oxide coated with dextran in the present invention.

The X-ray diffraction (XRD) pattern for the dextran coated nanoceria is shown in FIG. 4. The diffraction peaks found in the coated nanoceria are in a good agreement with those found in bulk ceria and preparation of uncoated nanoceria, as determined by the earlier investigator (W. Chengyun et al, 2002, S. Sathyamurthy et al, 2005). The broadening of the peak suggests that the particles are of small dimension. The particle size, which can be calculated using the Scherrer equation, is around 3 nm, which is in agreement with the data obtained by TEM. Also XRD confirms that it has (111), (220), (311) and (331) plane which was compared with the data obtained the JCPDF file.

Figure 5:
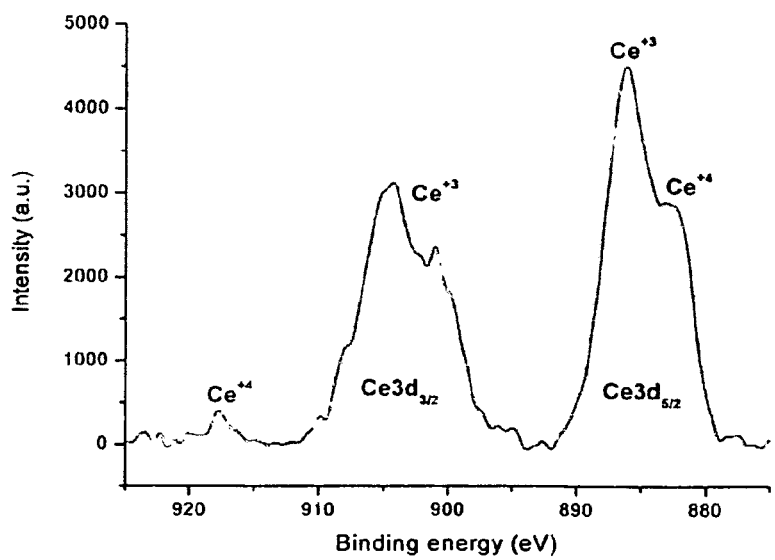
FIG. 5 shows the X-ray photon spectroscopy spectrum of the synthesized cerium oxide nanoparticles coated with dextran showing the presence of a mixed valence (Ce3+ and Ce4+) state.

X-ray photon spectroscopy (XPS) data in FIG. 5 show the presence of a mixed valence state, indicating that the dextran coating on the nanoparticle does not affect this key physical property of nanoceria. The data also show that the amount of $Ce^{+3}$ ion in the nanoparticle is more than the amount of $Ce^{+4}$ ion, in agreement with the small particle size (of less than 5 nm) as reported by D. Schubert et al., *Biochemical and Biophysical Research Communications* 2006, 342, 86.

FIG. 6A is a photographic image of a sample of dextran nanoceria in aqueous solution wherein the vial on the left corresponds to a solution of dextran nanoceria obtained following the procedure we are disclosing in this invention disclosure, after ultrafiltration with an Amicon 30 K filter as described in Example 1. When a sample of this solution is concentrated using a 30K Centricon concentrator, a more concentrated dextran coated nanoceria is obtained, as shown in FIG. 6B, the vial on the right, with a darker solution. No precipitation of agglomeration is observed in any of the two solutions, showing the great stability of this nanoceria preparation in aqueous solution.

Figure 7A:
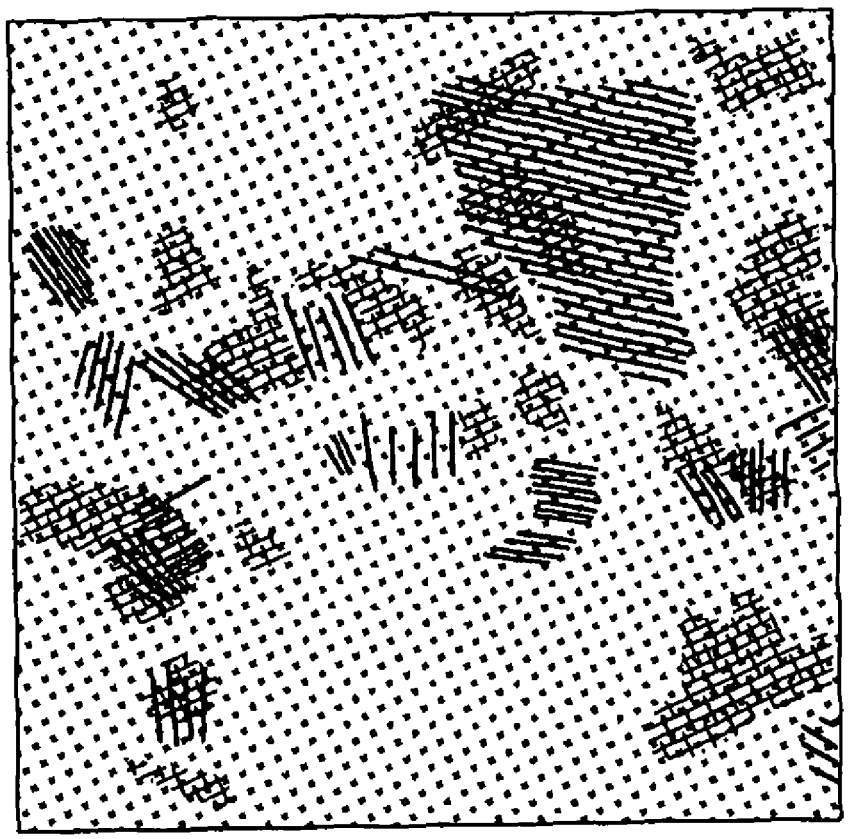
FIG. 7A is a transmission electron microscopy (TEM) image of the dextran coated ceria nanoparticles showing the size and dispersity of the ceria crystals.
Figure 7B:
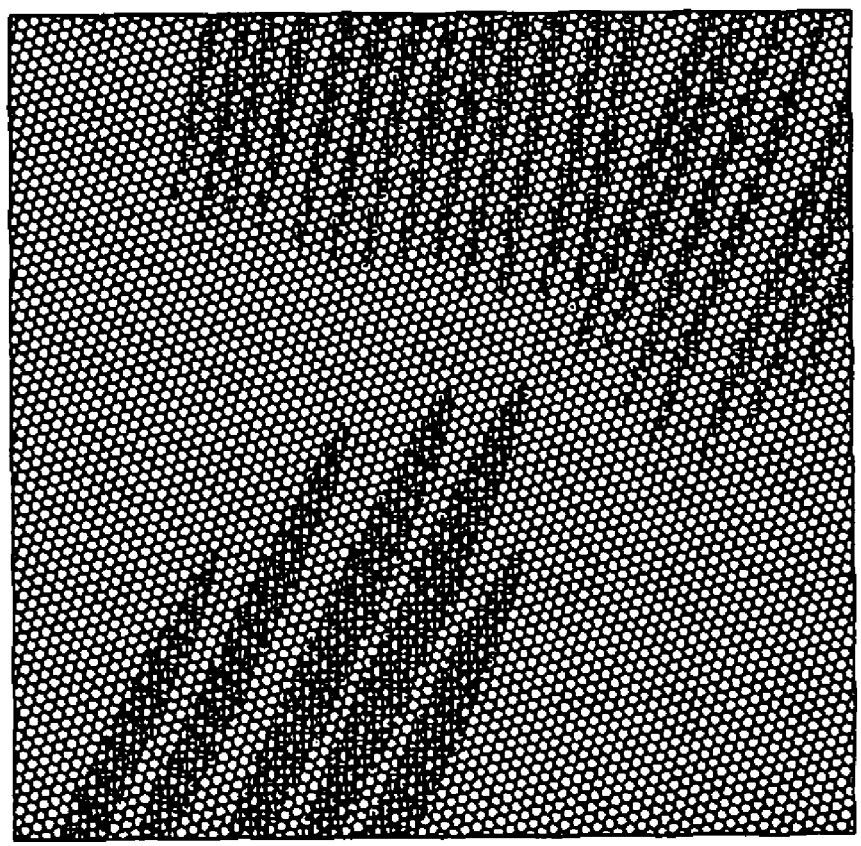
FIG. 7B is a high resolution transmission electron microscopy (HRTEM) image of the dextran coated ceria nanoparticles showing that the coating does not affect the crystallinity.
Figure 7C:
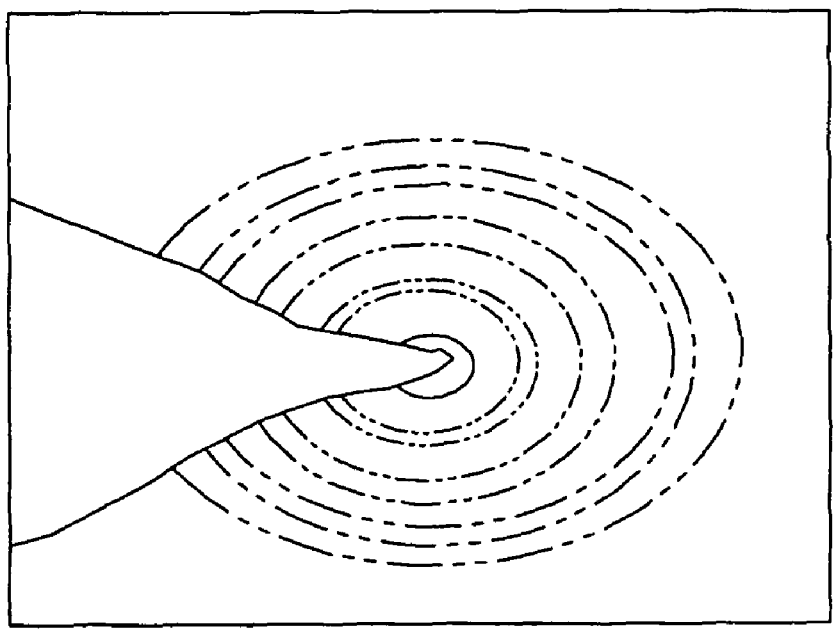
FIG. 7C is a selected area electron diffraction (SAED) image of a single ceria crystal showing that the dextran coated ceria crystal is a face-centered cubic (FCC) phase crystal.

Further characterization of the dextran coated nanoceria preparation is provided in FIGS. 7A, 7B and 7C showing the high crystallinity of the nanoceria particles of the present invention. FIG. 7A is a transmission electron microscopy (TEM) image of the dextran coated ceria nanoparticles showing the size and dispersity of the ceria crystals. FIG. 7B is a high resolution transmission electron microscopy (TEM) image of the dextran coated ceria nanoparticles, showing that the coating does not affect the crystallinity. FIG. 7C is a selected area electron diffraction (SAED) image of a single ceria crystal showing that the dextran coated ceria crystal is a FCC phase crystal.

Concanavalin studies were used to verify the dextran coating of the ceria nanoparticles of the present invention.

Figure 8:
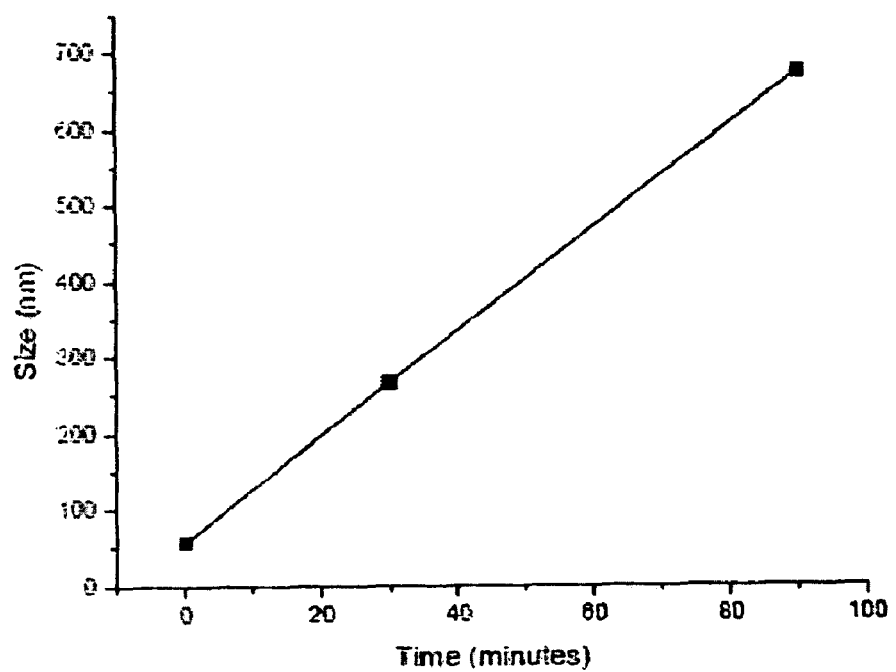
FIG. 8 is a graph showing the increase in particle size with time on concanavalin addition.

Concanavalin is a protein with four binding sites, known to bind carbohydrates. This protein has been used to induce the clustering of dextran-coated gold nanoparticles and most recently it was used in clustering iron oxide nanoparticles. It is used to study how the clustering phenomenon changes the optical (gold nanoparticles), or magnetic (iron oxide) properties of the nanoparticles. It is used to verify whether the dextran is associated to (coating) the nanoparticle. In these studies, dextran coated nanoceria is incubated with concanavalin and an increase in the particle size is observed as measured by dynamic light scattering (DLS). This increase in "size" by light scattering is not due to an increase in the size of the nanoparticles, but rather is due to the clustering of the nanoparticles in solution. FIG. 8 shows that after 90 minutes incubation with concanavalin, nanoparticle clusters of 650 nm in size are observed thus, showing the increase in particle size with time on concanavalin addition.

Figure 9:
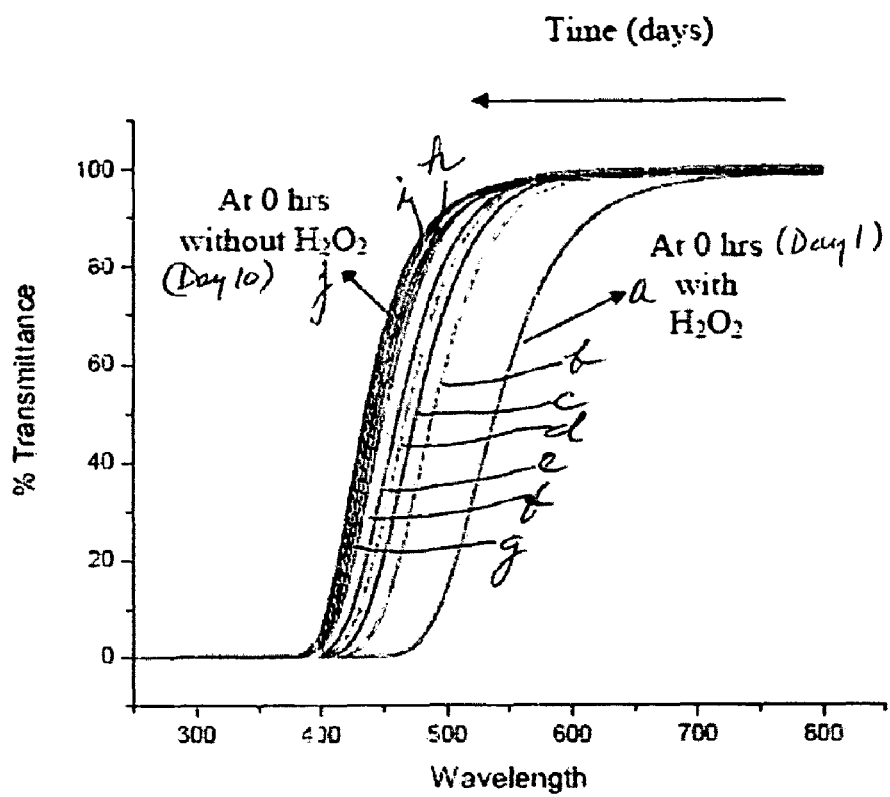
FIG. 9 is a graph showing reversible and successive shift in transmittance of dextran coated nanoceria particles after adding hydrogen peroxide (Days 1-10).

Autocatalytic behavior of dextran-coated nanoceria was studied with addition of hydrogen peroxide. One of the most interesting properties of nanoceria is its autocatalytic behavior. The ability of these nanoparticles to reversibly switch from $Ce_{+3}$ to $Ce_{+4}$, is a key factor for their biological applications as an antioxidant, among others. Therefore, it is determined whether the dextran coating on the nanoceria preparation compromised its autocatalytic behavior. In these experiments, the nanoparticles are oxidized using hydrogen peroxide. It is observed that after adding hydrogen peroxide to the nanoceria there is a red shift and also color changes to dark brown ($Ce_{+4}$). As the hydrogen peroxide decomposes from the nanoparticle suspension, the observed brown color starts to disappear and the solution color returns to yellow ($Ce_{+3}$) within ten days as shown in FIG. 9. In FIG. 9, note the reversible and successive shift in transmittance of dextran coated nanoceria particles after adding hydrogen peroxide on day one a, % transmittance plotted against the wavelength, is between approximately 475 nm to approximately 700 nm, at day 2 b, % transmittance is between approximately 410 nm to approximately 600 nm, day 3 c, % transmittance is between 400 nm and approximately 550 nm; days 4-10 d-j, after the addition of hydrogen peroxide and the decomposition of hydrogen peroxide nears completion, the plot of the % transmittance against wave length is within a narrower range between approximately 400 nm and approximately 450 nm wavelength, confirming the disappearance of the brown color.

Autocatalytic activity is represented Equation (1) below:

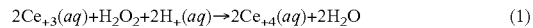

$$2Ce_{+3}(aq)+H_2O_2+2H_+(aq)\rightarrow 2Ce_{+4}(aq)+2H_2O \qquad (1)$$

FIGS. 10A-10F are real-time images of dextran coated nanoceria solutions with and without hydrogen peroxide. FIG. 10A shows a dextran-coated nanoceria solution without hydrogen peroxide on the left 5 and with hydrogen peroxide on the right 10 at day one. FIG. 10B shows a dextran-coated nanoceria solution without hydrogen peroxide on the left 15 and with hydrogen peroxide on the right 20 at day three. FIG. 10C shows dextran nanoceria solutions without hydrogen peroxide on the left 25 and with hydrogen peroxide on the right 30 at day seven. FIG. 10D shows dextran nanoceria solutions without hydrogen peroxide on the left 35 and with hydrogen peroxide on the right 40 at day ten. FIG. 10E shows dextran nanoceria solutions without hydrogen peroxide on the left 45 and with hydrogen peroxide on the right 50 at day ten after adding fresh hydrogen peroxide on the tenth day. FIG. 10F shows dextran nanoceria solutions without hydrogen peroxide on the left 55 and with hydrogen peroxide on the right 60 at day twenty. The real-time images confirm the autocatalytic activity shown in FIG. 9; there are color changes as the hydrogen peroxide decomposes from contact with the nanoparticle suspension.

With regard to biological activity, preliminary biological data shows that, as expected, the dextran-coated nanoceria preparation act as potent antioxidant agents. In these experiments, normal human cell cultures are exposed to hydrogen peroxide. This treatment causes a high level of cellular stress, similar to that experienced by cells under oxidative damage. The data show that in the absence of dextran nanoceria (DNC), from approximately 50% to approximately 95% of the cells died upon addition of hydrogen peroxide, whereas most of them survive this harsh treatment when in the presence of dextran coated nanoceria (DNC).

Figure 11A:
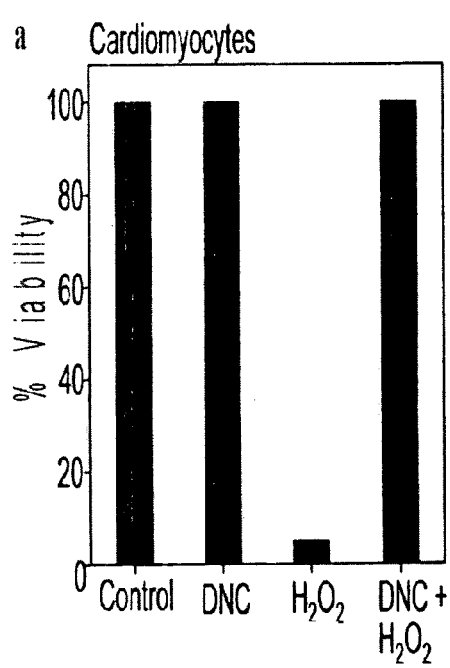
FIG. 11A is a graph showing the percent viability of normal cardiomyocyte cell cultures untreated and treated with dextran coated nanoparticles, hydrogen peroxide and a combination of dextran coated nanoparticles and hydrogen peroxide.
Figure 11B:
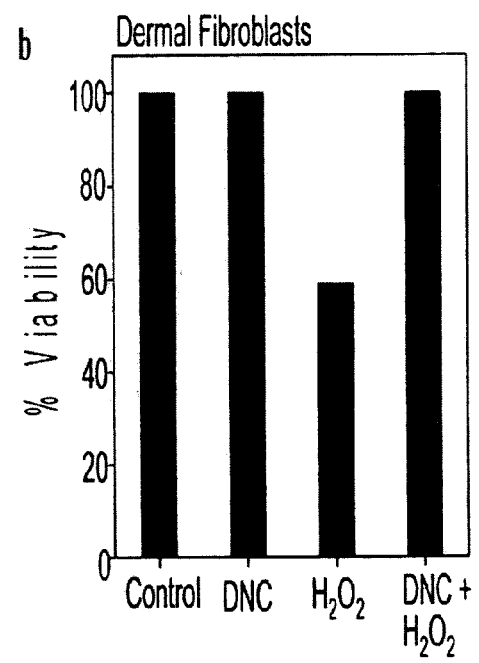
FIG. 11B is a graph showing the percent viability of normal dermal fibroblasts cell cultures untreated and treated with dextran coated nanoparticles, hydrogen peroxide and a combination of dextran coated nanoparticles and hydrogenperoxide.

FIGS. 11A and 11B are graphs of percent viability of normal cell cultures, cardiomyocytes and dermal fibroblast, respectively. In FIGS. 11A and 11B, the control is untreated and thus 100% viable; the cells treated with dextran coated nanoceria (DNC) are 100% viable and the cells treated with a combination of dextran coated nanoparticles (DNC) and hydrogen peroxide are 100% viable. However, FIG. 11A shows that normal cell cultures of cardiomyocytes are approximately 5% viable when treated with or exposed to only hydrogen peroxide and FIG. 11B shows that normal cell cultures of dermal fibroblasts are approximately 50% viable when treated with hydrogen peroxide without dextran coated ceria nanoparticles (DNC). Thus, FIGS. 11A and 11B are graphical illustrations of the effectiveness of dextran coated ceria nanoparticles as potent antioxidant agents that promote 100% cell viability in the presence of deadly oxidizing agents.

The crosslinking and amination of dextran coated ceria with epichlorohydrin as discussed in Example 2 above, was studied to determine whether the anti-oxidant properties of the nanoceria particles could be extended to injectable or targetable biomedical applications.

The dextran coated nanoceria prepared according to Example 1 shows great stability in water and various aqueous buffers, such as 0.1 M phosphate buffer, pH 7.4, without compromising its autocatalytic and antioxidant properties. However, the surface of this nanoparticle cannot be easily modified with targeting ligands such as peptides, oligonucleotides and proteins. To advance these studies, the polymeric dextran coating has been crosslinked on the surface of the ceria nanoparticle using epichlorohydrin and further derivatized its surface with ammonia to yield an aminated dextran coated nanoceria. As discussed earlier, it is known in the art to use other crosslinking agents and the present invention incorporates by reference, other known crosslinking agents, such as, but not limited to, glutaraldehyde, bromide derivatives of cyanogens, and the like.

Preliminary characterization of this preparation shows that indeed the dextran surface contains reactive amino groups that can be used to conjugate targeting ligands and various dyes, including near infrared dyes that would allow in vivo optical tracking of the nanoparticle. Furthermore, this amine group, which has a positive charge at physiological pH, can be reacted with a succinic anhydrate, resulting in a carboxylated or negatively charged nanoceria preparation, greatly expanding the conjugation capabilities of the aminated preparation.

Figure 12:
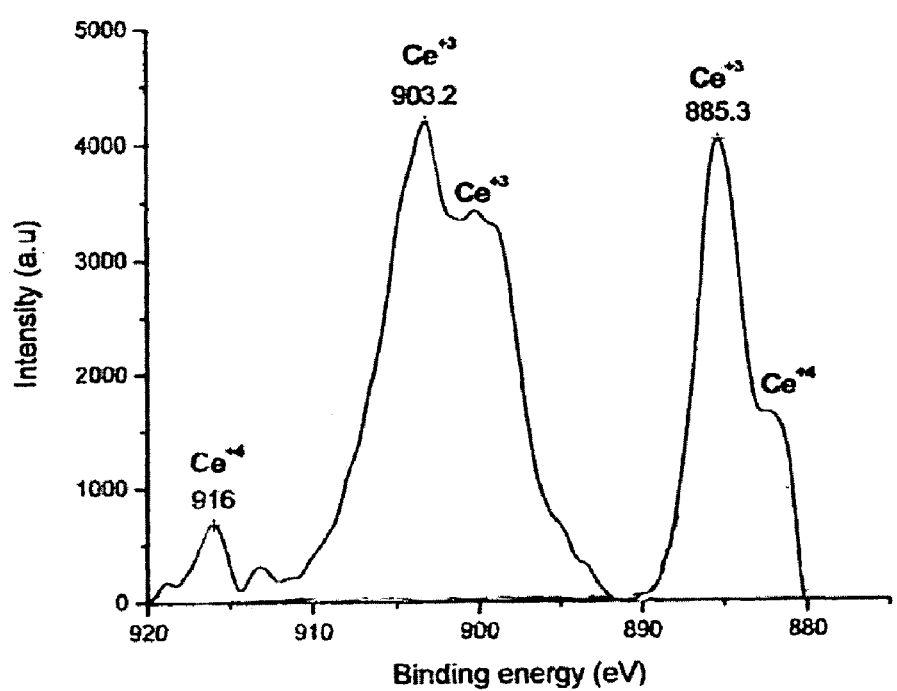
FIG. 12 is an X-ray photon spectroscopy (XPS) spectra of the aminated nanoceria showing the presence of a mixed valence, $Ce^{+3}$ and $Ce^{+4}$ similar to the spectrum of dextran coated nanoceria that is not aminated.

FIG. 12 is an X-ray photon spectroscopy (XPS) spectrum of the aminated crosslinked nanoceria showing the presence of a mixed valence, $Ce^{+3}$ and $Ce^{+4}$ similar to the spectrum of dextran coated nanoceria that is not aminated.

Physical properties of the aminated dextran coated nanoceria were analyzed by X-ray photon spectroscopy to determine whether the crosslinking procedure would affect the presence of both $Ce_{+3}$ and $Ce_{+4}$ and therefore its biological and autocatalytic activity. As shown in FIG. 12, the presence of both $Ce_{+3}$ and $Ce_{+4}$ species in the aminated dextran coated nanoceria are similar to those obtained with non-crosslinked nanoceria. This indicates that crosslinking of the dextran does not affect the dual valency ($Ce_{+3}/Ce_{+4}$) in the nanoceria preparation of the present invention and most likely will not affect its autocatalytic/antioxidant properties. Biological uses of the crosslinked, biodegradable polymer-coated nanoceria include administration to human and other mammals needing antioxidant treatments to prolong cell life.

Example 3

Carboxylated Polymer Coating of Nanoceria Particles

In another embodiment, following the procedure outlined in Example 1, wherein under ambient conditions, a 1 molar solution of a polyacrylic acid is used in place of the 1 molar solution of dextran, nanoceria particles are coated with a biodegradable polymer containing a plurality of carboxylic groups (carboxylated polymer), wherein a portion of the carboxyl groups are associated with the cerium oxide surface and a portion of carboxyl groups are exposed on the nanoparticle surface and available for conjugation. The carboxylated nanoparticle can be reacted with a diamine, such as ethylene diamine, and correspondingly converted to an amine functionalized nanoparticle.

Synthesis Method.

The preparation of polyacrylic acid coated nanoceria (PAA-nanoceria) involves the use of cerium (III) nitrate and polyacrylic acid (PAA). 1 M cerium (III) nitrate (Aldrich, 99%) solution (2.17 grams in 5.0 milliliters (ml) of water) was mixed with 0.5 mM solution of PAA (Sigma) to form mixture (I). With continuous stirring, the cerium nitrate and PAA mixture (I), is added drop wise to 30.0 ml of 29% ammonium hydroxide (Sigma Aldrich, 30%) solution to form mixture II. Subsequently, mixture (II) is stirred continuously for 24 hours; at this point, the solution has changed from a light yellow to a deep brown color. Next, the stirred mixture (II) is centrifuged at 4000 rpm for two 30 minute cycles to settle down any debris and large particles. The centrifuged solution is then purified from free PAA by ultrafiltration using 30K molecular weight cut-off Amicon filter (Millipore, Inc.) The resulting negative charge on the PAA-nanoceria is assessed by zeta potential analysis.

Below is a schematic diagram (2) of the synthesis of polyacrylic acid coated nanoceria (PAA-nanoceria).

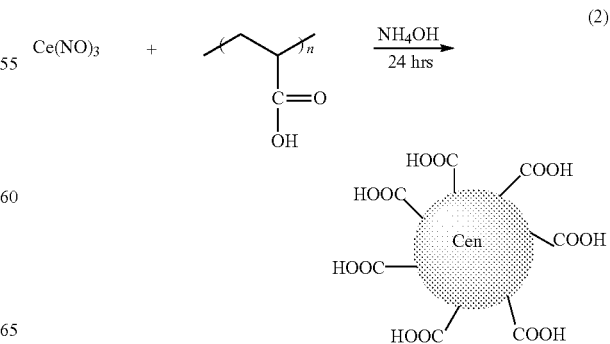

Note that the nanoparticles are functionalized with carboxylic groups on the surface, which allows conjugation of peptides, DNA oligonucleotides, proteins, antibodies and small molecules for targeting applications, without the need for cross-linking the polymer.

Furthermore, the carboxylic groups on the polyacrylic acid nanoceria can be converted to reactive amine groups by the reaction with a water soluble diamine, such as ethylene diamine, in the presence of a water soluble carbodiimide as disclosed in Gaw et al., U.S. Patent Publication 2002/0124194 for coating of iron oxide nanoparticles as MRI contrast agents.

Figure 13:
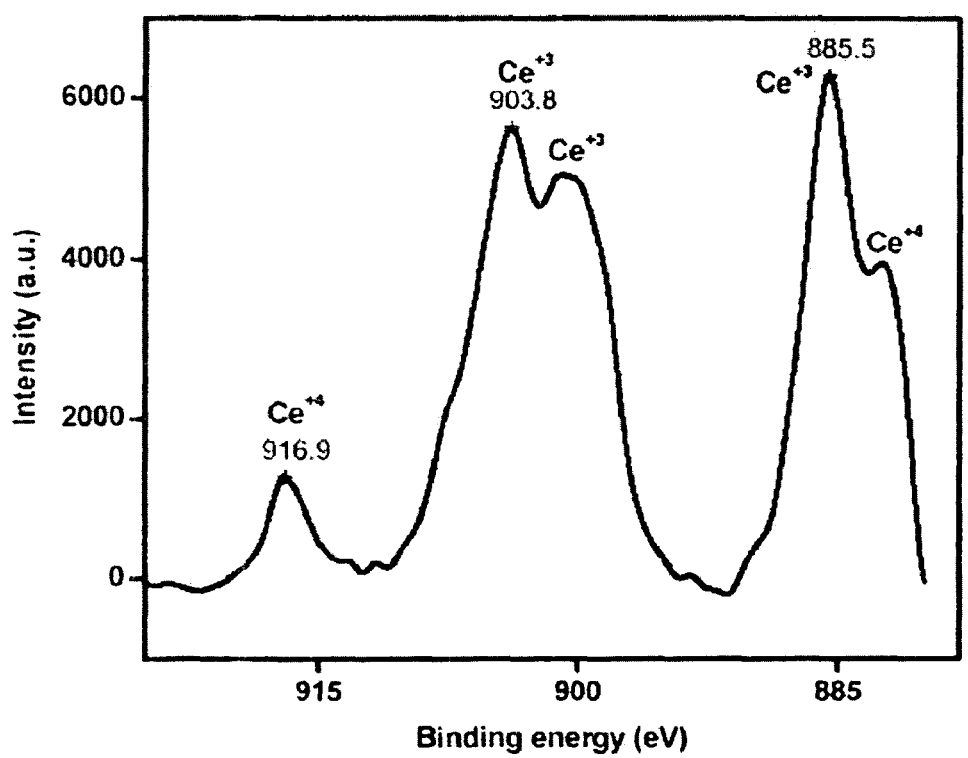
FIG. 13 is an X-ray photon spectroscopy (XPS) spectrum of the polyacrylic acid coated nanoceria (PAA-nanoceria) showing the presence of a mixed valence, $Ce^{+3}$ and $Ce^{+4}$ similar to the spectrum of dextran coated nanoceria and aminated dextran coated nanoceria shown in FIG. 12.

PAA-nanoceria possess similar autocatalytic activity as regular, non-coated nanoceria, dextran coated nanoceria, and aminated dextran coated nanoceria. In addition, PAA-nanoceria contains both $Ce^{4+}$ and $Ce^{3+}$ (mixed valance) on the nanoparticle which is important for its autocatalytic and antioxidant activity as shown in FIG. 13. The X-ray photon spectroscopy (XPS) image of polyacrylic acid coated nanoceria (PAA-nanoceria) in FIG. 13 is substantially similar to the X-ray photon spectroscopy (XPS) image of dextran coated nanoceria and aminated dextran coated nanoceria shown in FIG. 12. This indicates that the PAA-nanoceria will behave like the other polymer coated nanoceria preparations disclosed herein.

Prior to the present invention, a facile, cost effective, non-toxic synthesis of biodegradable polymer coated nanoceria particles was not available. The synthesis does not require surfactants or vigorous experimental conditions and the end-product is suitable for unlimited biomedical applications.

Prior to the present invention, it was not known that a biodegradable polymeric coating of ceria nanoparticles would not affect the autocatalytic and antioxidant properties of the ceria nanoparticles.

A biodegradable polymer coated nanoceria exhibits good solubility and stability in water and phosphate buffer saline. The preparation has good stability over many days in the buffer solutions which is advantageous over the preparations which aggregate when redispersed in aqueous media. This characteristic makes them suitable for biomedical applications and clinical use. Further, there is no problem with agglomeration in aqueous solution over a long period of time, as with preparations using a sol-gel technique as reported by H. S. Potdar et al. in *Materials Chemistry and Physics,* 2002 74, 306.

Further advantages of the biodegradable polymer coated cerium oxide nanoparticle include a suspension that can be concentrated using ultrafiltration devices without agglomeration of the nanoparticles.

With regard to the second embodiment, the dextran coating on the nanoparticle can be crosslinked with epichlorohydin and ammonia, resulting in an aminated dextran coated ceria nanoparticles. The major benefit of the crosslinked dextran coating is the ability to form conjugates to various ligands, such as peptides, antibodies, DNA-oligonucleotides, proteins and small molecules, to create a targetable ceria nanoparticle. This would allow targeting or "homing" of the nanoparticle to the corresponding site of inflammation or disease.

All embodiments of the present invention are useful in forming colloidal compositions which include nanoparticle suspensions of cerium oxide coated with a biodegradable polymer. The resulting colloidal composition is highly stable in water and water-based buffers, such as phosphate saline buffer and the like. The colloidal compositions are also suitable for concentration and sterilization by filtration.

Similar procedures have been used in the preparation of carboxylated coated iron oxide nanoparticles, allowing for the creation of targeted molecular imaging agent for MRI as reported in Gaw et al. U.S. Patent Publication 2003/0124,194; the teaching with regard to use of carboxylated polymers is incorporated herein by reference.

Some dextran coated iron oxide nanoparticles have been approved by the FDA for various applications including MRI imaging of lymph nodes as reported by M. G. Harisinghani, et al. in *New England Jl. of Medicine* 2003, 348, 2491.

The newly developed synthesis of biodegradable polymer coated ceria nanoparticles presented herein would be ideal for clinical applications and a candidate for FDA approval. It was an unexpected finding that the physical properties of the biodegradable polymer coated ceria nanoparticles remain unaffected by the polymeric coating which substantially improves handling and application for antioxidant and autocatalytic biomedical applications.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method for the synthesis of a plurality of polymer-coated cerium oxide nanoparticles coated with a biodegradable polymer for antioxidant, free-radical scavenger and autocatalytic biomedical applications, comprising the steps of:
   a) preparing an aqueous cerium nitrate solution containing approximately 2.0 to approximately 3.0 grams of cerium nitrate to approximately 5 ml of water;
   b) mixing the aqueous cerium nitrate solution with a biodegradable polymer to form mixture (I);
   c) adding mixture (I) dropwise to an ammonium hydroxide solution while continuously stirring to form mixture (II);
   d) centrifuging the mixture (II) containing ammonium hydroxide to settle any debris or large particles;
   e) purifying the centrifuged mixture of d) by ultrafiltration;
   f) recovering a plurality of non-agglomerated, polymer-coated cerium oxide nanoparticles coated with the biodegradable polymer wherein the plurality of polymer-coated cerium oxide nanoparticles has a UV profile exhibiting strong absorption below approximately 400 nm with peak absorption at approximately 300 nm; and
   g) contacting isolated biological cells with the plurality of polymer-coated cerium oxide nanoparticles wherein the antioxidant, free-radical scavenging and autocatalytic properties of the polymer-coated cerium oxide nanoparticles are unchanged from uncoated cerium oxide nanoparticles.

2. The method of claim 1, wherein the biodegradable polymer is selected from the group consisting of a carbohydrate polymer, a synthetic polyol, a carboxylated polymer, and derivatives thereof.

3. The method of claim 2, wherein the carboxylated polymer is polyacrylic acid.

4. The method of claim 2, wherein the carboxylated polymer is reacted with a diamine selected from at least one of ethylene diamine, propylene diamine and hexane diamine, to provide an aminated cerium oxide nanoparticle in a reaction that eliminates the need for polymer crosslinking.

5. The method of claim 2, wherein the carbohydrate polymer is a polysaccharide.

6. The method of claim 5, wherein the polysaccharide is selected from the group consisting of dextran, arabinogalactan and chitosan.

7. The method of claim 6, wherein the polysaccharide is dextran.

8. A composition of matter that is useful as a potent antioxidant in biomedical applications that comprises:
a plurality of polymer-coated nanoceria particles in contact with isolated biological cells wherein the plurality of polymer-coated nanoceria particles is coated with a biodegradable polymer selected from at least one of a carbohydrate polymer, a synthetic polyol, a carboxylated polymer, and derivatives thereof wherein the plurality of polymer-coated cerium oxide nanoparticles has a UV profile exhibiting strong absorption below approximately 400 nm with peak absorption at approximately 300 nm and the antioxidant properties of the polymer-coated cerium oxide nanoparticles are unchanged from uncoated cerium oxide nanoparticles.

9. The composition of claim 8, wherein the carboxylated polymer is polyacrylic acid and derivatives thereof.

10. The composition of claim 8, wherein the carbohydrate polymer is a polysaccharide and derivatives thereof.

11. The composition of claim 10, wherein the polysaccharide is selected from the group consisting of dextran, arabinogalactan, chitosan and derivatives thereof.

12. The composition of claim 11, wherein the polysaccharide is dextran and derivatives thereof.

13. The composition of claim 12, wherein the plurality of dextran-coated cerium oxide nanoparticles has a UV profile exhibiting strong absorption below approximately 400 nm with peak absorption at approximately 300 nm.

14. The composition of claim 12, wherein the physical properties of the dextran-coated cerium nanoparticles replicate the physical properties of the uncoated nanoceria particles for therapeutic applications as an antioxidant, free-radical scavenger and autocatalytic agent.

15. The composition of claim 12, wherein the plurality of dextran-coated cerium oxide nanoparticles form a colloidal suspension that is stable in water.

16. The composition of claim 12, wherein the plurality of dextran-coated cerium oxide nanoparticles form a colloidal suspension that is stable in a phosphate buffer saline solution.

17. A composition of matter that is useful as an antioxidant, free-radical scavenger and autocatalyst in biomedical applications that comprises:
a plurality of polymer-coated nanoceria particles in contact with isolated biological cells wherein the plurality of polymer-coated nanoceria particles is coated with a crosslinked-aminated biodegradable polymer selected from at least one of a carbohydrate polymer, a synthetic polyol, a carboxylated polymer, and derivatives thereof wherein the plurality of crosslinked-animated polymer-coated cerium oxide nanoparticles has a UV profile exhibiting strong absorption below approximately 400 nm with peak absorption at approximately 300 nm and the antioxidant, free-radical scavenging and autocatalytic properties of the polymer-coated cerium oxide nanoparticles are unchanged from uncoated cerium oxide nanoparticles.

18. The composition of claim 17, wherein the carbohydrate polymer is a polysaccharide.

19. The composition of claim 18, wherein the polysaccharide is selected from the group consisting of dextran, arabinogalactan and chitosan.

20. The composition of claim 19, wherein the polysaccharide is dextran.

21. The composition of claim 20, wherein the plurality of dextran-coated cerium oxide nanoparticles has a UV profile exhibiting strong absorption below approximately 400 nm with peak absorption at approximately 300 nm.

22. The composition of claim 20, wherein the physical properties of the dextran-coated cerium nanoparticles replicate the physical properties of the uncoated nanoceria particles for therapeutic applications as an antioxidant, free-radical scavenger and autocatalytic agent.

23. The composition of claim 20, wherein the plurality of dextran-coated cerium oxide nanoparticles form a colloidal suspension that is stable in water.

24. The composition of claim 20, wherein the plurality of dextran-coated cerium oxide nanoparticles form a colloidal suspension that is stable in a phosphate buffer saline solution.

25. A composition of matter that is useful as an antioxidant, free-radical scavenger and autocatalyst in biomedical applications that comprises:
a plurality of polymer-coated nanoceria particles in contact with mammalian cells in need of antioxidant treatments to prolong cell life wherein the plurality of polymer-coated nanoceria particles is coated with a crosslinked-aminated biodegradable polymer selected from at least one of a carbohydrate polymer, a synthetic polyol, a carboxylated polymer, and derivatives thereof wherein the plurality of crosslinked-animated polymer-coated cerium oxide nanoparticles has a UV profile exhibiting strong absorption below approximately 400 nm with peak absorption at approximately 300 nm and the antioxidant, free-radical scavenging and autocatalytic properties of the polymer-coated cerium oxide nanoparticles are unchanged from uncoated cerium oxide nanoparticles.

\* \* \* \* \*

UNITED STATES PATENT AND TRADEMARK OFFICE
CERTIFICATE OF CORRECTION

| | | |
|---|---|---|
| PATENT NO. | : 8,333,993 B1 | Page 1 of 1 |
| APPLICATION NO. | : 11/965343 | |
| DATED | : December 18, 2012 | |
| INVENTOR(S) | : Jesus Manuel Perez | |

It is certified that error appears in the above-identified patent and that said Letters Patent is hereby corrected as shown below:

Col. 1, line 15 insert the following:

-- STATEMENT REGARDING FEDERALLY SPONSORED RESEARCH OR DEVELOPMENT

This invention was funded in part by NIH, grant number 5K01CA101781. The government has certain rights in this invention. --

Signed and Sealed this
Twelfth Day of February, 2013

Teresa Stanek Rea
*Acting Director of the United States Patent and Trademark Office*

UNITED STATES PATENT AND TRADEMARK OFFICE
CERTIFICATE OF CORRECTION

PATENT NO.         : 8,333,993 B1
APPLICATION NO.    : 11/965343
DATED              : December 18, 2012
INVENTOR(S)        : Jesus Manuel Perez It is certified that error appears in the above-identified patent and that said Letters Patent is hereby corrected as shown below:

Col. 1, line 15 insert the following:

-- STATEMENT REGARDING FEDERALLY SPONSORED RESEARCH OR DEVELOPMENT

This invention was made with Government support under Agency contract K01 CA101781 awarded by the National Institutes of Health. The Government has certain rights in this invention. --

This certificate supersedes the Certificate of Correction issued February 12, 2013.

Signed and Sealed this
Twenty-fifth Day of February, 2014

Michelle K. Lee
*Deputy Director of the United States Patent and Trademark Office*